United States Patent
Kim

(10) Patent No.: US 10,987,296 B2
(45) Date of Patent: Apr. 27, 2021

(54) **COMPOSITION FOR IMPROVING SKIN WRINKLE CONTAINING EXOPOLYSACCHARIDE PRODUCED BY *CERIPORIA LACERATA* AS ACTIVE INGREDIENT**

(71) Applicant: FUGENBIO CO., LTD., Seoul (KR)

(72) Inventor: Yoon Soo Kim, Seongnam-si (KR)

(73) Assignee: FUGENBIO CO., LTD., Seoul (KR)

( * ) Notice: Subject to any disclaimer, the term of this patent is extended or adjusted under 35 U.S.C. 154(b) by 289 days.

(21) Appl. No.: 15/750,555

(22) PCT Filed: Aug. 12, 2016

(86) PCT No.: PCT/KR2016/008919
§ 371 (c)(1),
(2) Date: Feb. 6, 2018

(87) PCT Pub. No.: WO2017/026855
PCT Pub. Date: Feb. 16, 2017

(65) Prior Publication Data
US 2019/0008748 A1    Jan. 10, 2019

(30) Foreign Application Priority Data
Aug. 13, 2015  (KR) .................. 10-2015-0114900

(51) Int. Cl.
| | | |
|---|---|---|
| *A61Q 19/02* | (2006.01) | |
| *A61Q 19/08* | (2006.01) | |
| *A61K 8/73* | (2006.01) | |
| *A61K 8/9728* | (2017.01) | |
| *A61Q 19/00* | (2006.01) | |
| *A61K 8/60* | (2006.01) | |

(52) U.S. Cl.
CPC .................. *A61K 8/73* (2013.01); *A61K 8/60* (2013.01); *A61K 8/9728* (2017.08); *A61Q 19/00* (2013.01); *A61Q 19/02* (2013.01); *A61Q 19/08* (2013.01)

(58) Field of Classification Search
None
See application file for complete search history.

(56) References Cited

U.S. PATENT DOCUMENTS

2014/0193454 A1*  7/2014  Kim ...................... A61K 36/07
                                                        424/195.15

FOREIGN PATENT DOCUMENTS

KR      10-1522415 B1    5/2015
KR         1522415  *    5/2015

OTHER PUBLICATIONS

Spravchikov et al. Diabetes, Jul. 2001, vol. 50, pp. 1627-1629.*
Cohen et al. International Journal of Medicinal Mushrooms, 16 (3): 273-291 (2014).*
Ji-Eun Kim et al., "Hyperglycemic Effect of Submerged Culture Extract of Ceriporia lacerata in Streptozotocin-induced Diabetic Rats", Food Science and Biotechnology, 2012, pp. 1685-1693, vol. 21, No. 6.
Korea Intellectual Property Office, Office Action for corresponding Korean Patent Application No. 10-2015-0114900, dated Oct. 21, 2016.
International Searching Authority, International Search Report for PCT/KR2016/008919, dated Nov. 1, 2016.

* cited by examiner

*Primary Examiner* — Vera Afremova
(74) *Attorney, Agent, or Firm* — Sughrue Mion, PLLC

(57) ABSTRACT

The present invention provides a composition and food for improving skin condition containing exopolysaccharides produced by *Ceriporia lacerata*, a mycelial culture fluid of *Ceriporia lacerata* comprising the exopolysaccharides, a dry powder of the mycelial culture fluid or an extract of the mycelial culture fluid as an active ingredient. The composition and the food for improving skin condition have a superior skin whitening effect, wrinkle improving effect, skin moisturizing effect or skin anti-aging effect.

16 Claims, 5 Drawing Sheets

[Fig. 1]
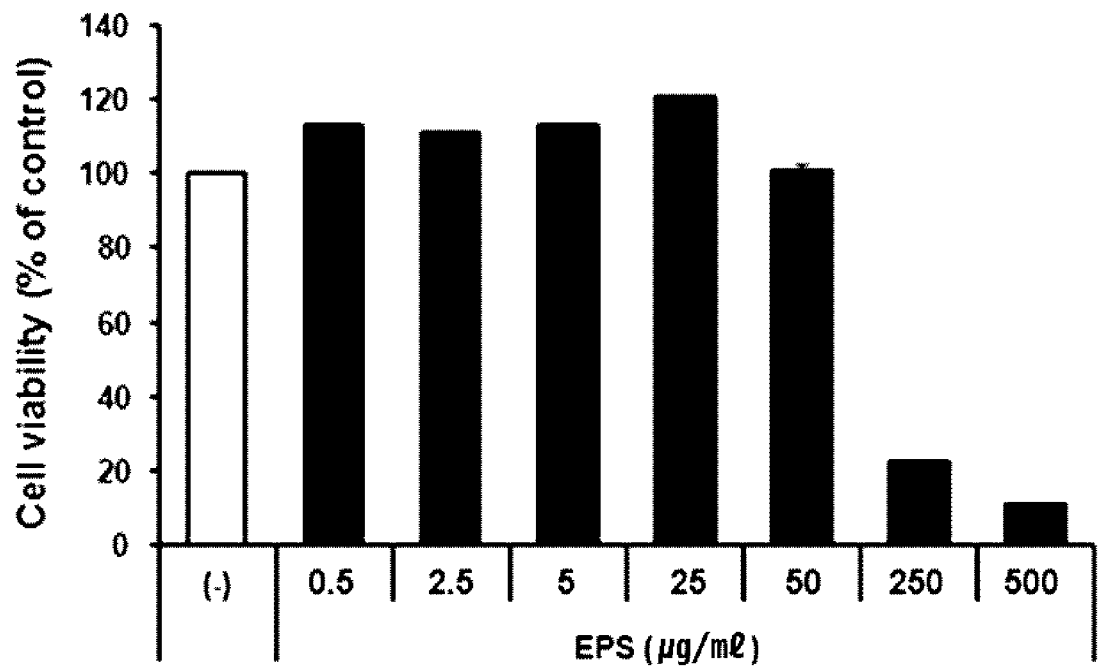
[Fig. 2]
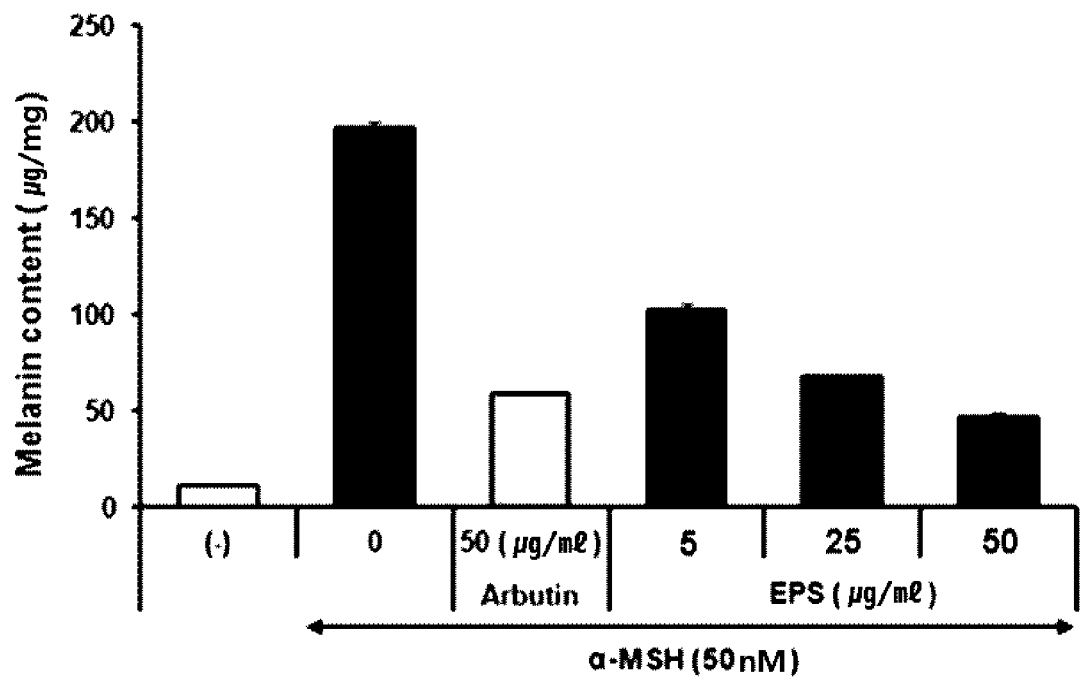

[Fig. 3]
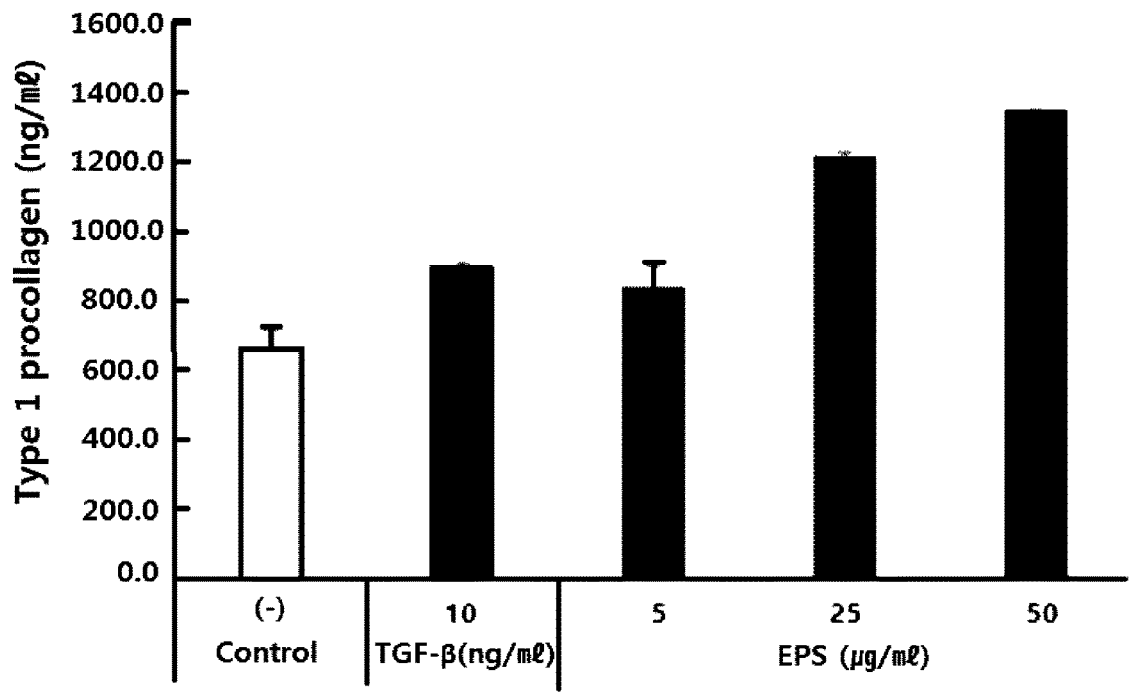
[Fig. 4]
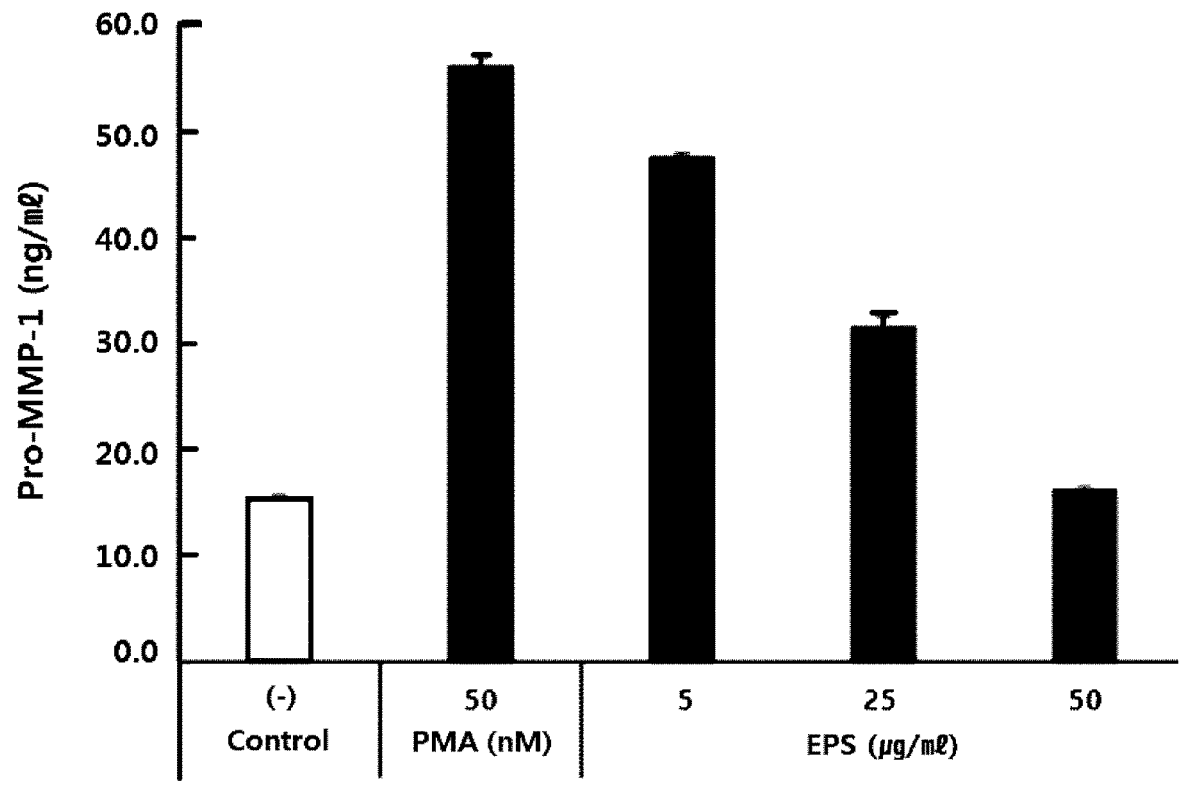

[Fig. 5]
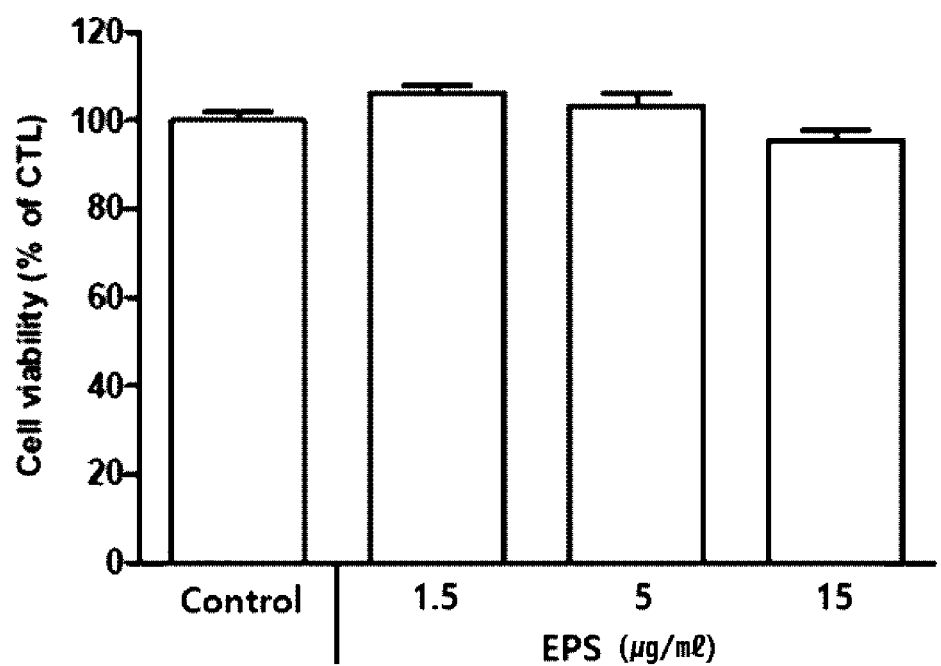

[Fig. 7]
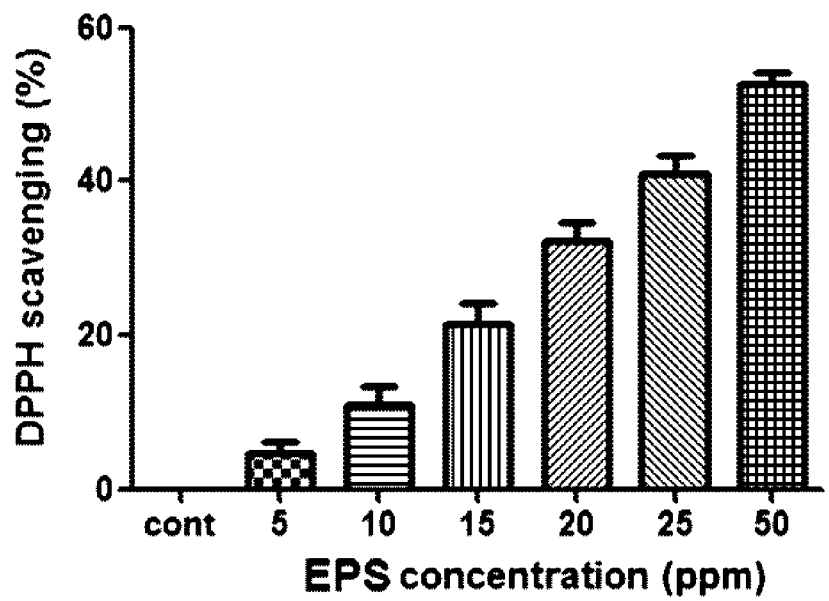
[Fig. 8]
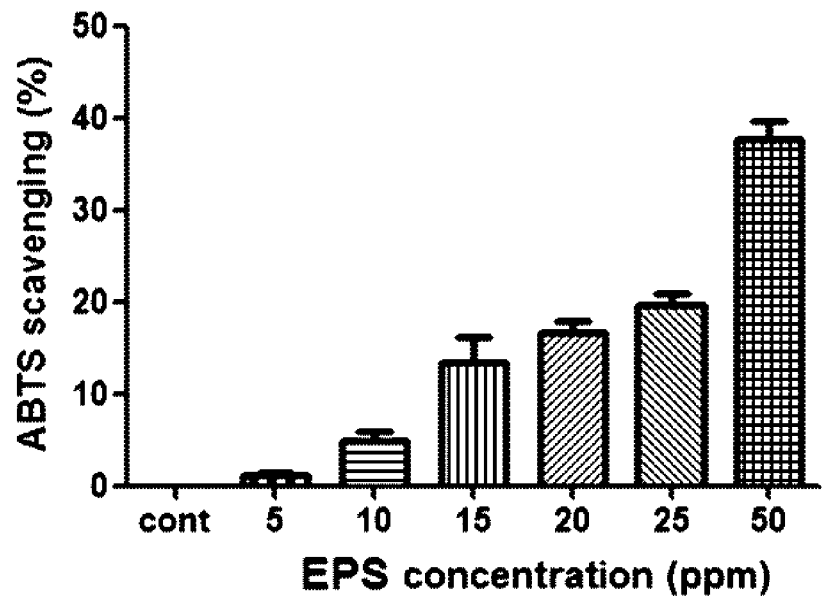

COMPOSITION FOR IMPROVING SKIN WRINKLE CONTAINING EXOPOLYSACCHARIDE PRODUCED BY *CERIPORIA LACERATA* AS ACTIVE INGREDIENT

CROSS REFERENCE TO RELATED APPLICATIONS

This application is a National Stage of International Application No. PCT/KR2016/008919 filed Aug. 12, 2016, claiming priority based on Korean Patent Application No. 10-2015-0114900 filed Aug. 13, 2015, the contents of all of which are incorporated herein by reference in their entirety.

TECHNICAL FIELD

The present invention relates to a composition and food for improving skin condition comprising an active ingredient produced by *Ceriporia lacerata*, a mycelial culture medium of *Ceriporia lacerata* containing the same, or dried powders or an extract of the mycelial culture medium, as an effective ingredient.

BACKGROUND ART

Skin is the primary preventive barrier of human body, which protects the organs in the body from external environmental stimuli and plays an important role in maintaining the body's homeostasis. However, as the skin gets old, the skin undergoes aging process progressively, resulting in the phenomena such as loss of skin elasticity, keratinization, wrinkle formation, and skin atrophy, etc.

Accordingly, there has been an attempt to promote collagen synthesis using retinoic acid and animal placenta-derived proteins, etc., as substances for improving skin condition, however, since retinoic acid is unstable, it is not only difficult to be formulated, but has limitation in terms of safety, while animal placenta-derived proteins have a fatal disadvantage that it could be from bovine extracts from cows with mad cow disease.

On the other hand, as whitening ingredients for skin beauty, substances which inhibit tyrosinase enzyme activity such as kojic acid and arbutin, etc., hydroquinone, vitamin C and derivatives thereof and various plant extracts have been used. However, the use of these substances is limited due to poor stability in a formulation resulting in coloration from decomposition, generation of foul odor, and uncertainty of their effects at in vivo level, etc.

It is known that *Ceriporia lacerata* is a kind of white-rotting fungus and conducts co-metabolism, i.e., lignin decomposition, in order to use carbon sources such as cellulose, hemi-cellulose, other polysaccharides, and glycerol, etc., in the ecosystem.

Regarding the use of *Ceriporia lacerata* in medical treatment, only the use of the extract of the culture medium of *Ceriporia lacerata* disclosed in Korean Patent No. 10-1031605 in the treatment of in diabetes is known so far. However, it has not been reported that *Ceriporia lacerata* has skin condition-improving effect using yet.

DISCLOSURE OF INVENTION

Technical Problem

Accordingly, the present inventors have found that an active ingredient isolated from *Ceriporia lacerata*, a mycelial culture medium of *Ceriporia lacerata* containing the same, or dried powders or an extract thereof shows an skin condition-improving effect, and have completed the present invention.

It is an object of the present invention to provide an active ingredient isolated from *Ceriporia lacerata*, and a composition and food for improving skin condition comprising the active ingredient.

It is another object of the present invention to provide a method for improving skin condition comprising administering an active ingredient produced by *Ceriporia lacerata*, and a use of an active ingredient produced by *Ceriporia lacerata* for preparing a composition for improving skin condition.

Solution to Problem

In accordance with one object of the present invention, there is provided a composition and food for improving skin condition comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium as an effective ingredient.

In accordance with another object of the present invention, there is provided a method for improving skin condition comprising administering an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium.

In accordance with another object of the present invention, there is provided a use of an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, for preparing a composition for improving skin condition.

Advantageous Effects of Invention

A composition and food comprising an extracellular polysaccharide produced by *Ceriporia lacerata*, a mycelial culture medium of *Ceriporia lacerata* containing the extracellular polysaccharide, dried powders or an extract of the mycelial culture medium as an effective ingredient according to the present invention shows excellent skin-whitening effect, wrinkle-improving effect, skin-moisturizing effect and skin anti-aging effect.

BRIEF DESCRIPTION OF DRAWINGS

FIG. 1 is a graph showing the cell viability after treatment of B16 melanoma cells with various concentrations of extracellular polysaccharides produced by *Ceriporia lacerata*.

FIG. 2 is a graph showing the amounts of melanin production after treatment of B16 melanoma cells with various concentrations of an extracellular polysaccharide produced by *Ceriporia lacerata*.

FIG. 3 is a graph showing the amounts of type-1 procollagen biosynthesis after treatment of human skin fibroblasts with extracellular polysaccharides produced by *Ceriporia lacerata* at various concentrations.

FIG. 4 is a graph showing the amounts of pro-collagenase (Pro-MMP-1, pro matrix metal protease-1) after treatment of human skin fibroblasts with extracellular polysaccharides produced by *Ceriporia lacerata* at various concentrations.

FIG. 5 is a graph showing the cell viability after treatment of keratinocytes with extracellular polysaccharides produced by *Ceriporia lacerata* at various concentrations.

FIGS. 6A, 6B and 6C are graphs showing filaggrin expression after treatment of keratinocytes with extracellular polysaccharides produced by *Ceriporia lacerata* at various concentrations, in which FIG. 6A and FIG. 6B represent mRNA and protein expressions of filaggrin, respectively, and FIG. 6C is a graph showing the quantified values of protein expression of filaggrin.

FIG. 7 is a graph showing DPPH (1,1-diphenyl-2-picrylhydrazyl) elimination activity of an extracellular polysaccharide produced by *Ceriporia lacerata*.

FIG. 8 is a graph showing ABTS (2,2'-azino-bis (3-ethylbenzothiazoline-6-sulfonic acid)) elimination activity of an extracellular polysaccharide produced by *Ceriporia lacerata*.

BEST MODE FOR CARRYING OUT THE INVENTION

Figure 6A:
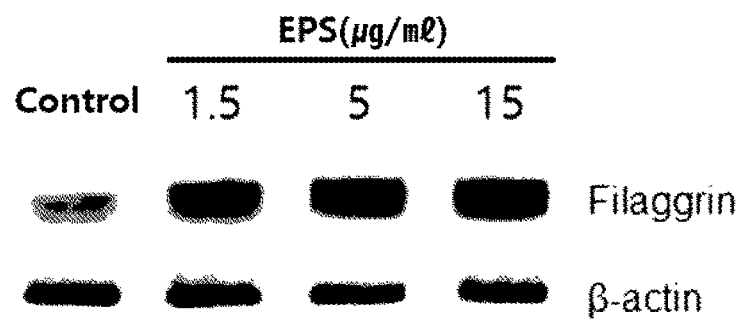

In the present invention, there is provided a composition for improving skin condition, which contains an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium as an effective ingredient.

As used herein, the term "extracellular polysaccharide (EPS)" refers to a part of the cell wall of a microorganism such as fungi, which means a polysaccharide secreted extracellularly to form a capsule around it, or a substance secreted as mucilage around cells or into media. The extracellular polysaccharide is secreted by microorganisms to protect themselves from the external environment such as antibodies, toxic substances, protozoa, and bacteriophages, etc.

In the above composition, the extracellular polysaccharide may comprise 40 to 60 wt % of sugar and 30 to 40 wt % of protein, 40 to 50 wt % of sugar and 32 to 38 wt % of protein, or 43 to 47 wt % of sugar and 33 to 36 wt % of protein, specifically about 45 wt % of sugar and about 34 wt % of protein.

The sugar may include mannose, galactose and glucose.

The extracellular polysaccharide may have a molecular weight of 100 to 150 kDa, 110 to 140 kDa or 115 to 125 kDa, more specifically about 120 kDa.

According to one embodiment of the present invention, the extracellular polysaccharide may be prepared by a preparation method comprising the steps of: (a) culturing mycelia of *Ceriporia lacerata* in a liquid to prepare a mycelial culture medium of *Ceriporia lacerata*, (b) drying the mycelial culture medium of *Ceriporia lacerata* to form powders, and (c) extracting the dried powders of the mycelial culture medium of *Ceriporia lacerata* with a solvent, and filtering and concentrating the resultant extract under reduced pressure.

The medium for culturing in a liquid in the step (a) may contain sugar, glucose, starch, sorghum powder, barley powder, soybean flour, magnesium sulfate ($MgSO_4$), monopotassium phosphate ($KH_2PO_4$), dipotassium phosphate ($K_2HPO_4$) and water, and the hydrogen ion concentration (pH) of the medium may be 4.5 to 6.0.

Specifically, the medium may contain 0.2 to 3 wt % of sugar, 0.2 to 3 wt % of glucose, 0.2 to 4 wt % of starch, 0.1 to 0.5 wt % of sorghum powder, 0.1 to 0.5 wt % of barley powder, 0.2 to 3 wt % of soybean flour, 0.01 to 0.1 wt % of magnesium sulfate ($MgSO4$), 0.01 to 0.25 wt % of monopotassium phosphate ($KH_2PO_4$), 0.01 to 0.25 wt % of dipotassium phosphate ($K_2HPO_4$) and residual quantity of water.

The culture in a liquid of the step (a) may be conducted under a blue LED light source, and may be conducted with a carbon dioxide concentration maintained at 1,000 to 2,000 ppm.

The culturing in a liquid, for example, may be conducted for 8 to 13 days at 20 to 25° C., under a blue LED light source, with the pH maintained at 4.5 to 6.0, an illuminance maintained at 0.1 to 0.8 LUX, an air injected at 0.5 to 2.0 $kgf/cm^2$, a carbon dioxide concentration maintained at 1,000 to 2,000 ppm. Specifically, the culture may be conducted under the condition of 20 to 25° C., pH 4.5 to 6.0, 0.5 to 2.0 $kgf/cm^2$, and carbon dioxide concentration of 1,000 to 2,000 ppm for 5 to 15 days. Culturing in a liquid under the above condition is preferable since it allows a high content of an extracellular polysaccharide produced.

The parent strain for use in step (a) may be a strain by culturing a dominant strain stored in PDA (Potato dextrose agar) medium at 1 to 5° C. in PDB (Potato dextrose broth) medium in Erlenmeyer flask using a shaking incubator at a constant temperature of about 25° C. for 7 to 9 days. In addition, the culture medium or obtained mycelium can be used as an inoculum after the parent strain is cultured as described above. Specifically, the amount of the mycelium to be inoculated may be about 0.5% (w/v) based on the solution to be cultured. Since a high amount of the mycelia (%/100 mL, w/v) does not necessarily result in a high content of the extracellular polysaccharide, the medium composition may be preferably selected such that it provides a condition for maximizing the content of extracellular polysaccharide, rather than the best nutritional ratio and environmental condition for the growth of mycelia.

The culture medium may be separated and purified into mycelia and an aqueous solution. For the separation and purification, the mycelia may be eliminated from the culture medium using a centrifuge and the remaining solution may be repeatedly purified using a Multi-Sheet Filter Press and a vibrating membrane separator (PALLSEP), followed by irradiation with UV rays for 1 minute. Also, the culture medium may be sealed and stored after removing oxygen, where the presence of mycelia in the medium may result in the change in the content of the effective ingredient due to the growth of the mycelia.

In the step (b), the mycelial culture medium prepared in the step (a) may be dried to form powders. In order to prevent the loss of an effective substance, the drying may be carried out at a temperature of 40° C. or lower, more specifically 30° C. or lower, for 48 to 96 hours. In addition, for the drying in step (b), a vacuum freeze dryer is preferably used rather than a vacuum dryer in which a relatively high evaporation temperature is set, in terms of minimizing the change in the content of the effective substance.

In the step (c), after the dried powders of a mycelial culture medium obtained in the step (b) are extracted with a solvent, an extracellular polysaccharide, an effective ingredient according to the present invention, is isolated.

Specifically, 100 ml of distilled water was added to 3 to 10 g of the dried powders of the mycelial culture medium and suspended well, followed by centrifugation at 5,000 to 10,000 rpm for 10 to 30 minutes to obtain a supernatant. And, then, a 2- to 3-fold amount of extraction solvent may be added to the supernatant, which may then be placed in a refrigerator at 1 to 5° C. and allowed to stand for 10 to 15 hours. The supernatant in the solution which had been allowed to stand may be obtained and centrifuged again at 5,000 to 10,000 rpm for 10 to 30 minutes, and the precipitate may be recovered, thereby preparing a crude extracellular polysaccharide. The crude extracellular polysaccharide may be vacuum freeze dried at 30° C. or lower to obtain a extracellular polysaccharide.

The extraction solvent may be a solvent selected from the group consisting of water, a lower alcohol having 1 to 4 carbon atoms, acetone, ether, chloroform and ethyl acetate or a mixture thereof, and more specifically, it may be a solvent selected from the group consisting of water, methanol, ethanol, butanol, acetone, and ethyl acetate or a mixture thereof, even more specifically, water or 50 to 80% (v/v) aqueous solution of ethanol.

The extracellular polysaccharide may be comprised in an amount of 0.1 to 80 wt %, specifically 0.1 to 50 wt %, based on the total weight of the composition for improving skin condition. And in the composition for improving skin condition, a mycelial culture medium of *Ceriporia lacerata*, dried powders thereof, or an extract of the mycelial culture medium may be adequately comprised in an amount which corresponds to the above amount of the extracellular polysaccharide. However, the effective content of an extracellular polysaccharide, a mycelial culture medium containing the extracellular polysaccharide, dried powder, or an extract of the mycelial culture medium may be adequately adjusted according to the method of use and purpose of the composition.

The composition for improving skin condition may have a skin-whitening, wrinkle-improving, skin-moisturizing or skin anti-aging effect.

The skin-whitening means the action of preventing or inhibiting a symptom resulting from the increase of melanin as the production of melanin is inhibited. According to one example, the composition of the present invention shows a skin-whitening effect by inhibiting the production of intracellular melanin, and has high stability, and shows very little side effects such as skin irritation, etc.

The wrinkle improvement may include prevention of wrinkles and removal of wrinkles. According to one example, the composition of the present invention can exert an excellent wrinkle-improving effect through molecular mechanisms such as inhibition of collagenase activity and promotion of collagen synthesis, etc.

The composition of the present invention is less irritating to the skin by using a biological agent, and has an excellent persistency of moisturizing effect by the excellent penetration ability to the skin and moisture retaining function in the stratum corneum. According to one example, the composition of the present invention promotes the expression of filaggrin, thereby exerting an excellent skin-moisturizing effect.

The composition of the present invention shows an antioxidative effect through free radical-elimination, and thus can be used for preventing or treating skin aging.

The composition according to the present invention shows very little toxicity and side effects in addition to having the above-mentioned effects, and thus can be safely used even when taken for a long time.

The composition for improving skin condition of the present invention may further comprise other publicly known compounds or plant extracts known to have a skin condition-improving effect. The publicly known compounds or plant extracts known to have a skin condition-improving effect may be, for example, mercaptosuccinic acid, mercaptodextran, teprenone, dihydroxy-isoquinoline, indomethacin, 3-hydroxymanule, vitamin K, thiazolidone, quinoline, lemon extract, cucumber extract, mulberry extract, licorice extract, rosemary extract, acerola cherry extract, ginkgo extract, carob extract and geranium extract, but is not limited to.

The skin condition-improving composition may be a cosmetic composition.

The cosmetic composition may be prepared into any formulations conventionally produced in the art. For example, the cosmetic composition may be formulated as a solution, a suspension, an emulsion, a paste, a gel, a cream, a lotion, a powder, a soap, a surfactant-containing cleansing, an oil, a powder foundation, an emulsion foundation, a wax foundation or spray. More specifically, it can be formulated into a soft lotion, a nutrition lotion, a nutrition cream, a massage cream, an essence, an eye cream, a cleansing cream, a cleansing foam, a cleansing water, a pack, a spray or a powder, but is not limited thereto.

The cosmetic composition may comprise any conventional ingredients generally used in cosmetics, for example, additives such as stabilizers, solubilizers, surfactants, vitamins, pigments and flavor, and carriers, in addition to an extracellular polysaccharide, a mycelial culture medium of *Ceriporia lacerata* containing the extracellular polysaccharide, dried powders of the mycelial culture medium, or an extract of the mycelial culture medium, which is an effective ingredient exhibiting skin condition-improving activity.

Furthermore, the present invention provides a food for improving skin condition, comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium as an effective ingredient.

Such extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium was as described above.

A food according to the present invention may be in the form of powders, granules, a tablet, a capsule or a drink, and may be a candy, a chocolate, a drink, a gum, a tea, a vitamin complex, a health supplementary food, and the like.

An extracellular polysaccharide, a mycelial culture medium containing the extracellular polysaccharide, dried powders of the mycelial culture medium, or an extract of the mycelial culture medium according to the present invention may be comprised in a food in an amount of 0.01 to 50 wt %, specifically 0.1 to 20 wt % based on the total weight of the food, and may be comprised in an amount of 0.02 to 10 g, specifically 0.3 to 1 g based on 100 mL of a drink.

The food may further comprise a sitologically acceptable food supplementary additive in addition to an extracellular polysaccharide, a mycelial culture medium of *Ceriporia lacerata* containing the extracellular polysaccharide, dried powders of the mycelial culture medium, or an extract of the mycelial culture medium.

The food for improving skin condition may have a skin-whitening, wrinkle-improving, skin-moisturizing or skin anti-aging effect. The food according to the present invention shows very little toxicity and side effects in addition to having the above-mentioned effects, and thus can be safely used even when taken for a long time.

The present invention provides a method for improving skin condition comprising administering an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium to a subject in need of improving skin condition.

The subject in need of improving skin condition may be a mammal, more specifically a human.

The extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium is as described above.

Mode for the Invention

Hereinafter, the present invention is explained in detail by Examples. The following Examples are intended to further illustrate the present invention without limiting its scope.

EXAMPLES

Preparation Example 1. Preparation of Culture Medium of *Ceriporia Lacerata*, Dried Powders Thereof, Extract, and Extracellular Polysaccharide (Exopolysaccharide; Hereinafter, Referred to as "EPS")

1-1: Preparation of Culture Medium of *Ceriporia Lacerata*

*Ceriporia lacerata* isolated from *Quercus serrata* collected at Sangju city, Gyeongbuk province were subcultured to obtain a parent strain, which was subsequently freeze-stored at −80° C., and the freeze-stored strain was cultured with 2 to 3 passages in PDA (Potato dextrose agar) medium (87 plastic bulbs, Difco, Becton Dickinson and Company), and the strain (hereinafter referred to as "PDA culture strain") was stored in a refrigerator at 4° C. until use. Then, 600 mL of the PDB (Potato dextrose broth) medium (Difco, Becton Dickinson and Company) was placed in an Erlenmeyer flask, and then a PDA culture strain was added thereto and shake-cultured at 25° C. for 8 days to obtain a PDB culture strain.

Meanwhile, for the culture of the strain, a liquid culture medium containing 1.5 wt % of sugar, 0.5 wt % of glucose, 0.5 wt % of potato starch, 0.25 wt % of sorghum powder, 0.25 wt % of barley powder, 0.75 wt % of soybean flour, 0.05 wt % of magnesium sulfate ($MgSO_4$), 0.05 wt % of monopotassium phosphate ($KH_2PO_4$), 0.05 wt % of dipotassium phosphate ($K_2HPO_4$) and residual quantity of water was sterilized for 20 minutes in a 800 L fermenter with the air injected at 1.5 $kgf/cm^2$ at 121° C. And then, the medium was cooled to 23° C., and inoculated with 600 mL of the PDB culture strain as a starter, and *Ceriporia lacerata* mycelia were liquid-cultured in the medium for 10 days at a constant temperature of 23° C., under a blue LED light source, with the air injected at 0.5 to 1.5 $kgf/cm^2$, an illuminance of 0.5 LUX, and a carbon dioxide concentration of 2,000 ppm, to prepare the mycelial culture medium of *Ceriporia lacerata*.

1-2: Preparation of Dried Powders of Culture Medium of *Ceriporia Lacerata*

The mycelial culture medium of *Ceriporia lacerata* prepared in the Preparation Example 1-1 was freeze-dried by using a vacuum freeze dryer at 25° C. for 72 hours to form powders, to prepare dried powders of a mycelial culture medium of *Ceriporia lacerata*.

1-3: Preparation of Extract of Mycelial Culture Medium of *Ceriporia Lacerata*

5 g of dried powders of the mycelial culture medium of *Ceriporia lacerata* prepared in Preparation Example 1-2 was added to 100 mL of distilled water and sufficiently suspended, and then the resulting solution was centrifuged at 8,000 rpm for 20 minutes. And then the supernatant separated therefrom was mixed with a 2- to 3-fold amount of ethanol, and allowed to stand for 12 hours at 4° C. Thereafter, the resultant supernatant was taken and an extract of the mycelial culture medium of *Ceriporia lacerata* was prepared therefrom.

1-4: Preparation of EPS from Culture Medium of *Ceriporia Lacerata*

The extract of the mycelial culture medium of *Ceriporia lacerata* prepared in Preparation Example 1-3 was further centrifuged at 8,000 rpm for 20 minutes, and then the precipitate was recovered to obtain crude EPS. The crude EPS was vacuum freeze dried in a vacuum freeze dryer for 72 hours at 25° C. to obtain an EPS produced by *Ceriporia lacerata*.

Example 1. Evaluation of EPS Properties 1-1: Molecular Weight Measurement of EPS Using Gel Permeation Chromatography (GPC)

The EPS prepared in Preparation Example 1 was dissolved in a solution of 0.1 M $Na_2SO_4$/0.05 M $NaN_3$ (adjusted to pH 4 with glacial acetic acid) to a concentration of 1% (w/v), and then the mixture was centrifuged at 4,000 rpm for 0.5 hour, then the supernatant alone was isolated and filtered with a 0.45 μm syringe filter and analyzed by GPC.

The refractive index of the detector was used for the GPC analysis, and OHpak SB 805 HQ (Shodex, Japan) was used for the GPC column, and 0.1 M $Na_2SO_4$/0.05 M $NaN_3$ (adjusted to pH 4 with glacial acetic acid) was used for the mobile phase, which was allowed to flow at a flow rate of 1.0 mL/min. Standard curves were generated using dextrans (American Polymer Corporation, USA) with different molecular weights (130 kDa, 400 kDa, 770 kDa or 1200 kDa), and the molecular weight of EPS was measured using refractive index (RI) measuring instrument Knauer K-2310 (Germany). The measurement conditions are summarized in Table 1 below.

TABLE 1

| | Measurement of molecular weight |
|---|---|
| HPLC system | Knauer K-501 system |
| Column | OHpak SB 805 HQ (Shodex, Japan) |
| Mobile phase | 0.1M $Na_2SO_4$/0.05M $NaN_3$/pH 4 |
| Flow rate | 1.0 mL/min |
| Measuring instrument | RI (Knauer K-2310) |

As a result, the molecular weight of EPS of the present invention was about 120 kDa.

1-2: Measurement of Sugar and Protein Contents of EPS

The EPS prepared in Preparation Example 1 was subjected to secondary purification and treated with a protein-hydrolysis enzyme to measure sugar and protein contents.

Specifically, the primary-purified EPS (EPS prepared in Preparation Example 1) was dissolved in distilled water and centrifuged at 8,000 rpm for 20 minutes to separate the supernatant, and then a 2- to 3-fold amount of ethanol was added thereto. The mixture was placed in a refrigerator at 4° C. and allowed to stand for 12 hours. Thereafter, the resultant supernatant alone was centrifuged again at 8,000 rpm for 20 minutes, and the precipitate was recovered to obtain a secondary-purified EPS. And the secondary-purified EPS was dissolved in distilled water and treated with Alcalase, a protein-hydrolysis enzyme, at a concentration of 0.5% (w/v) at 50° C. for 30 minutes.

The sugar content was measured by the phenol-sulfuric acid method. Specifically, 25 µL of 80% (w/v) phenol was added to 1 mL of each of the samples diluted at various concentrations, and then 2.5 mL of sulfuric acid was added thereto. The mixture was cooled to room temperature, and then the sugar content was calculated by measuring the absorbance at 465 nm.

Also, the protein content was measured by BCA method (see Smith P K et al., *Analytical Biochemistry*, 150 (1): 76-85, 1985) and bovine serum albumin was used as a standard.

The sugar and protein contents measured as described above are shown in Table 2 below. The sugar content was 45 to 51 wt % and the protein content was 33 to 34 wt %.

TABLE 2

| | Yield (%) | Total sugar content (%) | Total protein content (%) |
|---|---|---|---|
| EPS | 1.22 ± 0.03 | 45.32 ± 1.41 | 34.17 ± 0.73 |
| Secondary-purified EPS | 0.78 ± 0.01 | 50.49 ± 0.52 | 33.50 ± 2.79 |
| Enzyme-treated EPS* | 0.24 ± 0.06 | 51.39 ± 1.32 | 34.61 ± 1.51 |

*Enzyme treatment: Alkalase 0.5%, 50° C., 30 minutes.
Each value represents mean ± SE (n ≥ 3).

As a result of analyzing sugar composition of EPS, it was found that EPS mainly contains mannose, galactose and glucose.

Example 2. Verification of Skin-Whitening Effect of EPS 2.1 Viability Test of B16 Melanoma Cells The cytotoxicity of the EPS of Preparation Example 1 was examined.

Specifically, B16 melanoma cells (purchased from: ATCC) cultured in DMEM (Dulbecco's modified Eagle's medium) containing 10% FBS and 1% penicillin/streptomycin were inoculated into a 96-well plate. 16 hours after the inoculation, when the cells were adhered to the plate, they were treated with the EPS prepared in Preparation Example 1 at a concentration of 0.5 µg/ml, 2.5 µg/ml, 5 µg/ml, 25 µg/ml, 50 µg/ml, 250 µg/ml or 500 µg/ml. And 2 hours later, the cells were treated with 50 nM of α-MSH (alpha-melanocyte stimulating hormone), a substance known to induce melanin production, in an incubator at 37° C., 5% $CO_2$. In a control group for comparison, the same treatment as described above was conducted except that EPS treatment was not conducted.

After 72 hours of culture, the medium was removed, and 100 µl of MTT (3-(4,5-dimethythiazol-2-yl)-2,5-diphenyltetrazolium bromide) solution was added the cells, which were then reacted at 37° C. for 3 hours. After the reaction was completed, the solution was removed, 100 µl of DMSO was added thereto to dissolve the stained cells, and then the absorbance was measured at 570 nm using an ELISA reader. Cell viability (%) was calculated as [absorbance in Experimental group/absorbance in control group]×100, and the results are shown in FIG. 1.

As shown in FIG. 1, the EPS according to the present invention did not show cytotoxicity up to the concentration of 50 µg/ml.

2.2 Melanin Synthesis Inhibition Test

In order to examine the skin-whitening effect of the EPS of Preparation Example 1, the changes in the amount of produced melanin was measured.

Specifically, B16 melanoma cells cultured by the same method as in Example 2.1 were inoculated into a 96-well plate. 16 hours after the inoculation, when the cells were adhered to the plate, Experimental group was treated with the EPS prepared in Preparation Example 1 at a concentration of 5 µg/ml, 25 µg/ml and 50 µg/ml, and a negative control group was not treated at all. A positive control group was treated with arbutin, which is known to inhibit tyrosinase and thereby inhibit melanin pigment formation, at a concentration of 50 µg/ml. Then, the cells were treated with 50 nM α-MSH and cultured in an incubator of 37° C., 5% $CO_2$ for 72 hours. After culturing, the cells collected using trypsin-EDTA were centrifuged at 5000 rpm for 10 minutes, to obtain cell pellets from which the supernatant was removed. After the protein extraction buffer (Bio-Rad, USA) was added to the collected cell pellet, the cells were lysed in ice for 40 minutes, and the supernatant was collected by centrifugation at 12,000 rpm for 10 minutes. After the supernatant was diluted and the protein assay kit solution (Bio-Rad, USA) was added thereto, the supernatant was reacted for 15 minutes at room temperature. After the reaction, the absorbance was measured at 595 nm using an ELISA reader.

Protein amounts were obtained by interpolation on the green standard curve using bovine serum albumin. After protein quantification, the cells were reacted at 60° C. for 1 hour and the absorbance was measured at 595 nm using an ELISA reader.

The measurement results are shown as the amount of produced melanin/amount of protein (µg melanin/mg protein) in FIG. 2.

As shown in FIG. 2, it was found that the EPS according to the present invention inhibited melanin production in a concentration-dependent manner, and specifically, the EPS according to the present invention had superior inhibition effect on melanin production as compared to arbutin, a positive control.

Example 3. Verification of Wrinkle-Improving Effect of EPS 3.1 Collagen Biosynthesis Promotion Effect Test In order to examine the skin wrinkle-improving effect of the EPS of Preparation Example 1, human skin fibroblasts were treated with the EPS of Preparation Example 1, and the degree of collagen biosynthesis was measured.

Specifically, human skin fibroblasts (purchased from: ATCC, USA) cultured in DMEM containing 10% FBS and 1% penicillin/streptomycin were inoculated into a 12-well plate and cultured for 3 days. Thereafter, when the cells were adhered to the plate, the cells were treated with TGF-β (10 ng/ml) and the EPS of Preparation Example 1 at a concentration of 5 μg/ml, 25 μg/ml or 50 μg/ml, while a negative control group was not treated at all, and a positive control group was treated with TGF-β (10 ng/ml) alone. 20 μl of each cell culture medium collected after 72 hours of culture and 10 μl of antibody-POD conjugate solution (Takara) were added to a 96-well plate and cultured at 37° C. for 3 hours. Each well was cleansed with 400 μl of PBS, and then added with 100 μl of a substrate solution (tetramethoxybenzyl, TMBZ) and cultured at room temperature for 15 minutes, and then added with 100 μl of 1 N sulfuric acid, which was mixed well. Then, the absorbance at 450 nm was measured using an ELISA reader to calculate the amount of type-1 procollagen biosynthesis. The results are shown in FIG. 3.

As shown in FIG. 3, it was found that the EPS of the present invention increased collagen synthesis in a concentration-dependent manner. Specifically, the EPS of the present invention had superior collagen biosynthesis promotion effect as compared to TGF-β, the positive control group, at a concentration of 25 μg/ml or higher.

3.2 Collagenase Activity Inhibition Test

In order to examine the skin wrinkle-improving effect of the EPS of Preparation Example 1, the inhibition effect on the activity of collagenase, which promotes wrinkle formation by decomposing collagen, was measured. In order to measure the inhibition degree on the activity of collagenase (MMP-1, matrix metal protease-1), human skin fibroblasts were treated with PMA (phorbol 12-myristate 13-acetate), a substance that activates collagenase, and then treated with EPS, and the amount of procollagenase (Pro-MMP-1, pro-matrix metal protease-1) was measured.

Specifically, human skin fibroblasts cultured in DMEM containing 10% FBS and 1% penicillin/streptomycin were inoculated in a 12-well plate and cultured for 3 days. Thereafter, when the cells were adhered to the plate, Experimental group was treated with 50 nM of PMA (nmol/l) and EPS at a concentration of 5 μg/ml, 25 μg/ml or 50 μg/ml, and a negative control group was not treated at all, and a positive control group was treated with PMA (50 nM) alone. After culturing for 22 hours, the cell culture medium was collected and the amount of procollagenase was measured using a Human Pro-MMP1 Quantikine ELISA kit (R & D Systems). The results are shown in FIG. 4.

As shown in FIG. 4, it was found that the procollagenase activity was inhibited as the treatment concentration of EPS of the present invention was increased. The results indicate that the EPS according to the present invention has an excellent wrinkle-improving effect.

Example 4. Verification of Skin-Moisturizing Effect of EPS

4.1 Measurement of Keratinocyte Viability

In order to examine skin-moisturizing effect of the EPS of Preparation Example 1, the keratinocyte viability was measured by MTT assay.

Specifically, a keratinocyte cell line (purchased from CLS, Germany) was inoculated into a 24-well plate at $1 \times 10^4$ cells and cultured for one day. Thereafter, Experimental group was treated with the EPS prepared in Preparation Example 1 at a concentration of 1.5 μg/ml, 5 μg/ml and 15 μg/ml, and a negative control group was further cultured for one day without any treatment. For the evaluation of cell viability, the cells were treated with MTT reagents at 1 mg/ml and then further cultured for 4 hours, and after removing the culture medium, the cells were treated with DMSO to elute insoluble MTT. The cytotoxicity was evaluated by measuring the absorbance at 540 nm and the results are shown in FIG. 5.

As shown in FIG. 5, the EPS according to the present invention showed no cytotoxicity up to the concentration of 15 μg/ml.

4.2 Measurement of Filaggrin Expression

To examine the skin-moisturizing effect of the EPS of Preparation Example 1, mRNA and protein expressions of the gene of filaggrin, a precursor protein of natural moisturizing factor (NMF) for skin moisturization, were measured.

Specifically, keratinocytes were aliquoted into a 24-well plate at $2 \times 10^5$ cells, and cultured for one day. Thereafter, Experimental group was treated with of the EPS prepared in Preparation Example 1 at 1.5 μg/ml, 5 μg/ml and 15 μg/ml, while a negative control group was cultured for 24 hours without any treatment.

After removing the supernatant from the cells cultured by the above method, RNA was extracted according to the manual using Eazy blue lysis reagent (iNtRON Biotechnology), and then reverse transcriptional polymerase chain reaction (RT-PCR) was performed according to the method provided in RT PreMix (Bioneer, Korea). As for primers, the primers for filaggrin (Macrogen, Korea) were used, and β-actin was used as an internal control for comparison of expression levels.

Figure 6B:
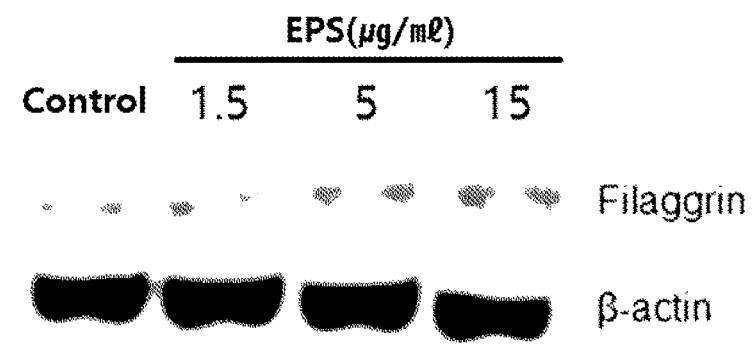
Figure 6C:
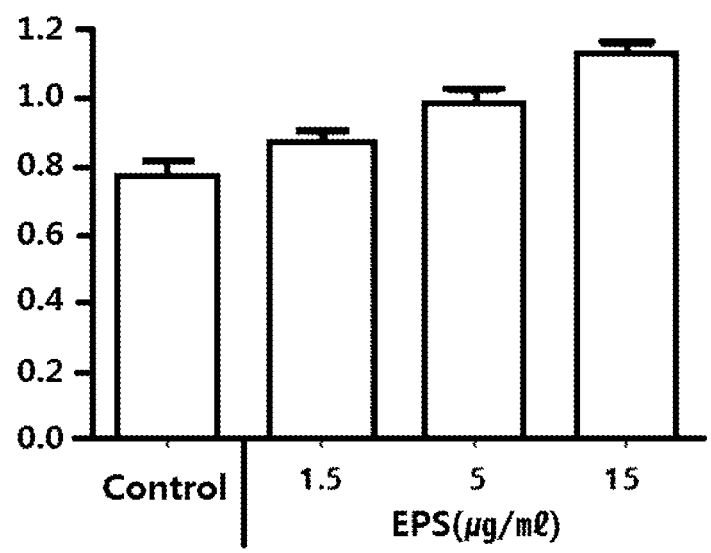

Further, in order to examine the expression level of filaggrin protein, the cells cultured by the above method were treated with Protein Extraction Solution (iNtRON Biotechnology) to dissolve the cells, which were then centrifuged to obtain supernatant. Then, the supernatant was diluted by adding proteins of the same amount, added with NuPAGE LDS sample buffer (Novex), and treated at 100° C. for 5 minutes. Then, after SDS-PAGE using Mini PROEAN® Tetra cell (Bio-Rad, USA), the proteins were transferred to Transfer membranes, and the bands were confirmed by Western blot. The results are shown in FIGS. 6A, 6B and 6C. FIGS. 6A and 6B show mRNA and protein expressions of filaggrin, respectively, and FIG. 6C is a graph showing the quantified values of protein expression of filaggrin.

As shown in FIGS. 6A, 6B and 6C, it was found that as the concentration of EPS of the present invention was increased, mRNA and protein expressions of filaggrin were promoted. The results show that the EPS according to the present invention has an excellent skin-moisturizing effect.

Example 5. Verification of Skin Anti-Aging Effect of EPS

5.1 Measurement of DPPH Free Radical-Elimination Activity

In order to examine the skin anti-aging effect of the EPS of Preparation Example 1, the antioxidative effect was verified by measuring the free radical-elimination activity using DPPH (1,1-diphenyl-2-picrylhydrazyl) (see Thaipong Kriengsak., et al., *Journal of Food Composition and Analysis*, vol. 19, pp. 669-675, 2006). The free radical-elimination activity was measured by a method in which the DPPH free radical was eliminated by an antioxidant of the sample, resulting in discoloration of the purple color, which is unique color of the radical.

Specifically, 2 ml of the EPS of Preparation Example 1 was added to each well of a 96-well plate at each concentration (5 ppm, 10 ppm, 15 ppm, 20 ppm, 25 ppm or 50 ppm), and then 198 ml of 100 mM DPPH solution was added thereto and mixed well, and the mixture was cultured at room temperature for 30 minutes. Then, in order to determine the amount of remaining DPPH, the absorbance at 540 nm was measured and thereby the DPPH radical-elimination activity was examined depending on the concentration. The same experiments were conducted twice, and the radical-elimination ratio (%) compared with the absorbance in the control group, which was treated with the same amount of PBS instead of the EPS of Preparation Example 1, is shown in Table 3 and FIG. 7. The radical-elimination ratio (%) was calculated as [1−(absorbance of mixed solution/absorbance of control group)]×100.

TABLE 3

| | DPPH free radical-elimination ratio (%) | | | | | |
|---|---|---|---|---|---|---|
| | Control | EPS 5 ppm | EPS 10 ppm | EPS 15 ppm | EPS 20 ppm | EPS 25 ppm | EPS 50 ppm |
| First experiment | — | 5.67 | 9.21 | 19.85 | 34.04 | 42.82 | 53.74 |
| Second experiment | — | 3.54 | 12.76 | 23.40 | 30.49 | 39.31 | 51.54 |
| Average | — | 4.61 | 10.99 | 21.63 | 32.27 | 41.07 | 52.64 |
| Standard deviation | — | 1.51 | 2.51 | 2.51 | 2.51 | 2.48 | 1.56 |

As shown in Table 3, it was confirmed that the DPPH free radical-elimination activity was gradually increased as the treatment concentration of EPS according to the present invention increased from 5 ppm to 50 ppm. Especially, when the treatment concentration of EPS was 50 ppm, the average DPPH free radical-elimination ratio was 52.64%. The above results indicate that the EPS according to the present invention shows a strong antioxidative activity, and thus has an excellent skin anti-aging effect.

5.2 Measurement of ABTS Free Radical-Elimination Activity

In order to examine the skin anti-aging effect of the EPS of Preparation Example 1, the antioxidative effect was verified by measuring the free radical-elimination activity using ABTS (2,2'-azino-bis(3-ethylbenzothiazoline-6-sulfonic acid)) (see Thaipong Kriengsak., et al., *Journal of Food Composition and Analysis*, vol. 19, pp. 669-675, 2006). The ABTS radical-elimination activity was measured by a method in which the ABTS free radical generated by a reaction with potassium persulfate was eliminated by an antioxidative substance of the sample, resulting in discoloration of the dark-green color, which is unique color of the radical.

Specifically, 2.6 mM potassium sulfate was mixed with 7.4 mM ABTS solution and allowed to react in a dark room for about 24 hours. The mixture was diluted with phosphate buffered saline to show an absorbance of 0.700±0.030 at 732 nm. Thereafter, EPS at the concentrations of 5 ppm, 10 ppm, 15 ppm, 20 ppm, 25 ppm and 50 ppm were added thereto and reacted for 10 minutes in a dark room. Then, in order to determine the amount of remaining ABTS, the absorbance at 732 nm was measured. The same experiments were conducted twice, and the radical-elimination ratio (%) obtained by comparing with the absorbance of the control group, which was treated with the same amount of PBS instead of the EPS of Preparation Example 1, was shown in Table 4 and FIG. 8. The radical-elimination ratio (%) was calculated as [1−(absorbance of sample/absorbance of control group)]×100.

TABLE 4

| | ABTS radical-elimination ratio (%) | | | | | |
|---|---|---|---|---|---|---|
| | Control | EPS 5 ppm | EPS 10 ppm | EPS 15 ppm | EPS 20 ppm | EPS 25 ppm | EPS 50 ppm |
| First experiment | — | 1.50 | 4.09 | 10.65 | 17.89 | 18.76 | 35.61 |
| Second experiment | — | 1.08 | 5.85 | 16.21 | 15.37 | 20.80 | 39.72 |
| Average | — | 1.29 | 4.97 | 13.43 | 16.63 | 19.78 | 37.67 |
| Standard deviation | — | 0.30 | 1.24 | 3.93 | 1.78 | 1.44 | 2.91 |

As shown in Table 4, it was confirmed that as the concentration of the EPS according to the present invention increased from 5 ppm to 50 ppm, more ABTS radicals in the samples gradually eliminated, resulting in the gradual decrease of the absorbance. Especially, when the concentration of the EPS was 50 ppm, the average ABTS radical-elimination ratio was 37.67%, which indicates a strong antioxidant activity. The above results show that the EPS according to the present invention has a strong antioxidative activity, and thus has an excellent skin anti-aging effect.

The invention claimed is:

1. A method of improving skin condition of a subject in need of such improvement, comprising administering a composition comprising
   an extracellular polysaccharide produced by *Ceriporia lacerata* mycelium;
   a mycelial culture medium of *Ceriporia lacerata*, said mycelial culture medium containing the extracellular polysaccharide;
   dried powders of the mycelial culture medium containing the extracellular polysaccharide; or
   an extract of the mycelial culture medium containing the extracellular polysaccharide, as an effective ingredient,
   wherein the skin condition improvement is wrinkle-improvement.

2. The method of claim 1, wherein the extracellular polysaccharide comprises 40 to 60 wt % of sugar and 30 to 40 wt % of protein, and has a molecular weight of 100 to 150 kDa.

3. The method of claim 2, wherein the extracellular polysaccharide comprises 43 to 47 wt % of sugar and 33 to 36 wt % of protein, and has a molecular weight of 115 to 125 kDa.

4. The method of claim 3, wherein the sugar contains mannose, galactose and glucose.

5. The method of claim 1, wherein the extracellular polysaccharide is prepared by a preparation method comprising the steps of:
   (a) culturing the *Ceriporia lacerata* mycelium in a liquid to prepare a mycelial culture medium of *Ceriporia lacerata*,
   (b) drying the mycelial culture medium of *Ceriporia lacerata* to form powders, and (c) extracting the powders of the mycelial culture medium of *Ceriporia lacerata* with a solvent, and filtering and concentrating the resultant extract under reduced pressure.

6. The method of claim 5, wherein the liquid of step (a) comprises a culture medium including sugar, glucose, starch, sorghum powder, barley powder, soybean flour, magnesium sulfate ($MgSO_4$), monopotassium phosphate ($KH_2PO_4$), dipotassium phosphate ($K_2HPO_4$) and water, and wherein a pH of the culture medium is 4.5 to 6.0.

7. The method of claim 5, wherein the culturing (a) is conducted under a blue LED light source with a carbon dioxide concentration maintained at 1,000 to 2,000 ppm.

8. The method of claim 1, wherein the extracellular polysaccharide is comprised in an amount of 0.1 to 80 wt % based on the total weight of the composition.

9. The method of claim 1, wherein the composition is a cosmetic composition for external use in a form selected from the group consisting of a solution, suspension, emulsion, paste, gel, cream, lotion, powder, soap, surfactant-containing cleansing, oil, powder foundation, emulsion foundation, wax foundation, and spray; wherein the cosmetic composition comprises a cosmetically acceptable additive; and wherein the composition is applied to a target site of skin of the subject.

10. The method of claim 9, wherein the cosmetic composition further comprises a plant extract.

11. The method of claim 10, wherein the plant extract is selected from the group consisting of mercaptosuccinic acid, mercaptodextran, teprenone, dihydroxy-isoquinoline, indomethacin, 3-hydroxymanule, vitamin K, thiazolidone, quinoline, lemon extract, cucumber extract, mulberry extract, licorice extract, rosemary extract, acerola cherry extract, ginkgo extract, carob extract, geranium extract, and a mixture thereof.

12. The method of claim 1, wherein the composition is a food or a dietary supplement, and comprises a sitologically acceptable food supplementary additive.

13. The method of claim 12, wherein the extracellular polysaccharide is comprised in an amount of 0.01 to 50 wt % based on the total weight of the food or the dietary supplement.

14. The method of claim 12, wherein the food or the dietary supplement is in a form of powders, granules, a tablet, a capsule or a drink.

15. The method of claim 12, wherein the food or the dietary supplement is a candy, a chocolate, a drink, a gum, a tea, or a vitamin complex.

16. The method of claim 1, wherein the skin condition improvement is mediated by inhibiting collagenase activity in the subject.

* * * * *